(12) United States Patent
Rose et al.

(10) Patent No.: US 9,603,574 B2
(45) Date of Patent: Mar. 28, 2017

(54) RECONFIGURABLE ELECTRONIC SUBSTRATE

(71) Applicant: GENERAL ELECTRIC COMPANY, Schenectady, NY (US)

(72) Inventors: James Wilson Rose, Guilderland, NY (US); Donna Marie Sherman, East Greenbush, NY (US); Jeffrey Scott Erlbaum, Albany, NY (US)

(73) Assignee: General Electric Company, Niskayuna, NY (US)

( * ) Notice: Subject to any disclaimer, the term of this patent is extended or adjusted under 35 U.S.C. 154(b) by 211 days.

(21) Appl. No.: 14/574,050

(22) Filed: Dec. 17, 2014

(65) Prior Publication Data

US 2016/0183365 A1 Jun. 23, 2016

(51) Int. Cl.
| | | |
|---|---|---|
| A61B 6/03 | (2006.01) | |
| A61B 6/00 | (2006.01) | |
| G10K 11/32 | (2006.01) | |
| G01R 33/34 | (2006.01) | |

(52) U.S. Cl.
CPC ............... *A61B 6/00* (2013.01); *A61B 6/032* (2013.01); *A61B 6/035* (2013.01); *G10K 11/32* (2013.01); *G01R 33/34007* (2013.01)

(58) Field of Classification Search
CPC ........ H05K 1/028; H05K 1/0286; G01T 1/17; G01T 7/00; A61B 6/035; A61B 6/4266; A61B 6/4233; A61B 6/032; A61B 6/00
USPC .......................................................... 73/649
See application file for complete search history.

(56) References Cited

U.S. PATENT DOCUMENTS

| | | | |
|---|---|---|---|
| 6,510,195 B1 | 1/2003 | Chappo et al. | |
| 7,010,088 B2 | 3/2006 | Narayanaswamy et al. | |
| 7,582,879 B2 | 9/2009 | Abenaim et al. | |
| 7,606,346 B2 | 10/2009 | Tkaczyk et al. | |
| 8,824,635 B2* | 9/2014 | Tkaczyk ................ | A61B 6/037 250/363.08 |
| 2004/0120448 A1* | 6/2004 | Ratzmann ............. | A61B 6/035 378/4 |
| 2005/0018810 A1* | 1/2005 | Narayanaswamy .... | G01T 1/249 378/91 |
| 2006/0231767 A1 | 10/2006 | Danzer et al. | |
| 2008/0165921 A1* | 7/2008 | Tkaczyk ................ | A61B 6/032 378/19 |
| 2008/0240339 A1* | 10/2008 | Du ........................ | A61B 6/032 378/5 |
| 2009/0129538 A1* | 5/2009 | Tkaczyk ................ | A61B 6/032 378/5 |
| 2011/0080993 A1* | 4/2011 | Hoffman ................ | A61B 6/032 378/19 |
| 2011/0080994 A1* | 4/2011 | Hoffman ................ | A61B 6/032 378/19 |
| 2011/0272588 A1 | 11/2011 | Jadrich et al. | |

(Continued)

FOREIGN PATENT DOCUMENTS

WO 2013176657 A1 11/2013

*Primary Examiner* — Helen Kwok
(74) *Attorney, Agent, or Firm* — Melissa K. Dobson (57) ABSTRACT

The present disclosure relates to the fabrication of electrical components and, in particular to the use of a reconfigurable substrate to which a flexible circuit may be affixed. In certain embodiments, the reconfigurable substrate may be moved between different configurations, certain of which are suitable for fabrication and certain of which are suitable for operation.

20 Claims, 10 Drawing Sheets

(56) References Cited

U.S. PATENT DOCUMENTS

| | | | |
|---|---|---|---|
| 2012/0181434 A1* | 7/2012 | Sawada | G01T 1/2002 |
| | | | 250/361 R |
| 2012/0183119 A1* | 7/2012 | Ikhlef | A61B 6/035 |
| | | | 378/19 |
| 2012/0193545 A1* | 8/2012 | Tkaczyk | G01T 1/24 |
| | | | 250/370.08 |
| 2014/0159226 A1 | 6/2014 | Bolognia | |
| 2015/0071401 A1* | 3/2015 | Lacey | G01N 23/046 |
| | | | 378/19 |

* cited by examiner

RECONFIGURABLE ELECTRONIC SUBSTRATE

BACKGROUND

The subject matter disclosed herein relates to the configuration and fabrication of electronic device, such as electronic devices employing flexible circuitry.

Conventional electronic devices are often fabricated using standardized and mass-produced circuitry elements, such as flex circuits, which may then be disposed in or on the overall electronic device. In certain instances, the disposition of the pre-produced circuitry elements within a device may not be subject to rigorous constraints, for example a flex circuit within a device may be constrained only where connections are made (typically the ends of the flex circuit) or may be minimally or loosely constrained as part of the fabrication of a larger electronic device.

Conversely, in other types of devices, the requirements placed on the placement and positioning of internal circuitry may be strict. Further, in some instances it may be desirable to have a particular, three-dimensional configuration of the circuitry element in the finally fabricated final product, but such a three-dimensional configuration may be inconsistent with the desired techniques to be used in fabricating the electronic device. Thus, in certain manufacturing contexts, the final configuration of the circuitry within a device may be inconsistent with the fabrication approaches that would otherwise be most useful in manufacturing the device.

BRIEF DESCRIPTION

In one embodiment, an electronic module is provided. The electronic module, in this embodiment, includes a first component having a first planar surface and one or more additional components rotatably attached to the first component. Each additional component comprises a second planar surface that is generally parallel to the first planar surface in a first configuration of the electronic module and is not parallel to the first planar surface in a second configuration of the electronic module. The electronic module further includes a flexible circuit laminated to both the first planar surface and the second planar surfaces. The flexible circuit comprises a first electrical component positioned over the first planar surface and a second electrical component positioned over at least one of the second planar surfaces such that, in the first configuration the first electrical component and the second electrical component are generally parallel to one another and in the second configuration the first electrical component and the second electrical component are not parallel to one another.

In a further embodiment, a method for fabricating an electronic module is provided. In accordance with this method, an electronic substrate that is in a first configuration is placed into a laminator tool. The electronic substrate comprises a first planar surface and a second planar surface that are generally parallel to one another when in the first configuration. A flexible circuit is positioned on the electronic substrate such that a first circuitry of the flexible circuit is on the first planar surface and a second circuitry of the flexible circuit is on the second planar surface. The flexible circuit is laminated onto the electronic substrate. The electronic substrate is removed from the laminator tool. The electronic substrate is reconfigured into a second configuration in which the first planar surface and the second planar surface are not parallel to one another.

In an additional embodiment, an imaging system is provided. The imaging system includes a signal detection component comprising one or more detector modules. Each detector module comprises: an electronic substrate movable between at least a first configuration and a second configuration, wherein the first configuration has two or more planar surfaces that are generally parallel to one another while in the second configuration the two or more planar surface are not parallel to one another; a flex circuit laminated onto the electronic substrate, wherein the flex circuit is laminated onto the two or more planar surfaces; and one or more alignment features present on the electronic substrate that mate with complementary features present in an interface with the signal detection component.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Alignment and placement of electronic circuitry as part of a fabrication process may be problematic in certain contexts, such as in contexts where a final three-dimensional configuration is desired that is different from an initial configuration that may be useful during fabrication. One problem currently faced in fabricating such a configuration is that no commercially available tools are designed to place a die on side facets of a substrate. One approach to addressing this absence involves placing the application specific integrated circuits (ASICs) on the flexible circuit prior to conforming the circuit to the substrate. However, this approach creates a substantial likelihood of damaging the ASICs in the conforming process.

With this in mind, aspects of the present disclosure relate to integration of electronics to a substrate (e.g., an alignment substrate) used in a final product where a non-planar topology of the substrate (e.g., a three-dimensional configuration) is desired. By way of example, a radiation (e.g., X-ray or gamma ray) detector is described herein as one example of an electronic device that might benefit from the presently disclosed approaches. However, it should be understood that any examples provided herein, including use in a detector device, are provided to provide—a real-world example and context and to, thereby, simplify explanation and description of the present approaches.

Figure 1:
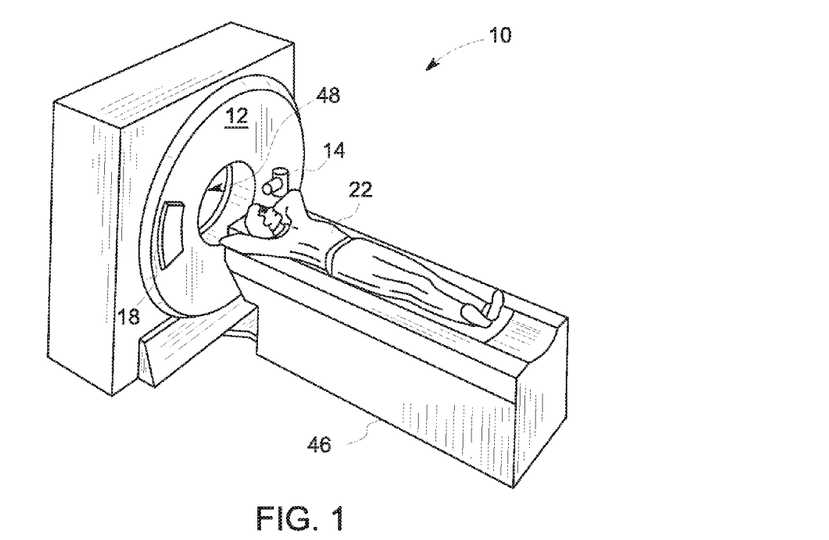
FIG. 1 is an isometric view of an exemplary CT imaging system, as may use a CT sensor array for medical imaging, in accordance with aspects of the present disclosure.

With this in mind, and turning to the figures, FIG. 1 depicts a computed tomography (CT) imaging system, components of which may benefit from the approach described herein. By way of example, components or modules of the sensor array may be fabricated as discussed herein. As used herein, a "sensor array" refers to a component comprising one or more individual sensors. In many configurations, a sensor array may itself include a component having, for example, a two-dimensional array of sensors, and a plurality of sensor arrays may be assembled into a larger assembly referred to as a "detector array." A "sensor array" may comprise an M×N array of sensors; wherein both M and N are integer numbers equal to or greater than one. Thus, the scope of the term "sensor array" is not intended to exclude devices having only one sensor.

By way of illustration, the description below refers to a CT imaging system. It is noted, however, that aspects of the present invention may be advantageously used in various other applications, which are limited neither to medical imaging applications nor to a CT modality. Examples of other modalities may be magnetic resonance, ultrasound, positron emission tomography, and a multi-energy computed tomography. Examples of other applications may be equipment inspections and diagnostics as may be performed in an industrial setting or security inspections as may be performed in a transportation setting, such as a baggage scanning for an airport or container inspection in a port, etc.

In some CT imaging system configurations, an X-ray source projects a fan-shaped beam which is collimated to lie within an X-Y plane of a Cartesian coordinate system and generally referred to as an "imaging plane". The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each sensor of the array produces a separate electrical signal that is a measurement of the beam intensity at the detector location. The intensity measurements from all the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements, i.e., projection data, from the detector array at one gantry angle is referred to as a "view". A "scan" of the object comprises a set of views made at different gantry angles, or view angles, during one revolution of the X-ray source and detector. To reduce the projection acquisition time, multi-slice CT has been introduced. In multi-slice CT, multiple rows of projection data are acquired simultaneously at any time instant using a multi-row detector, i.e., a detector array having multiple rows of detector elements or modules.

Figure 2:
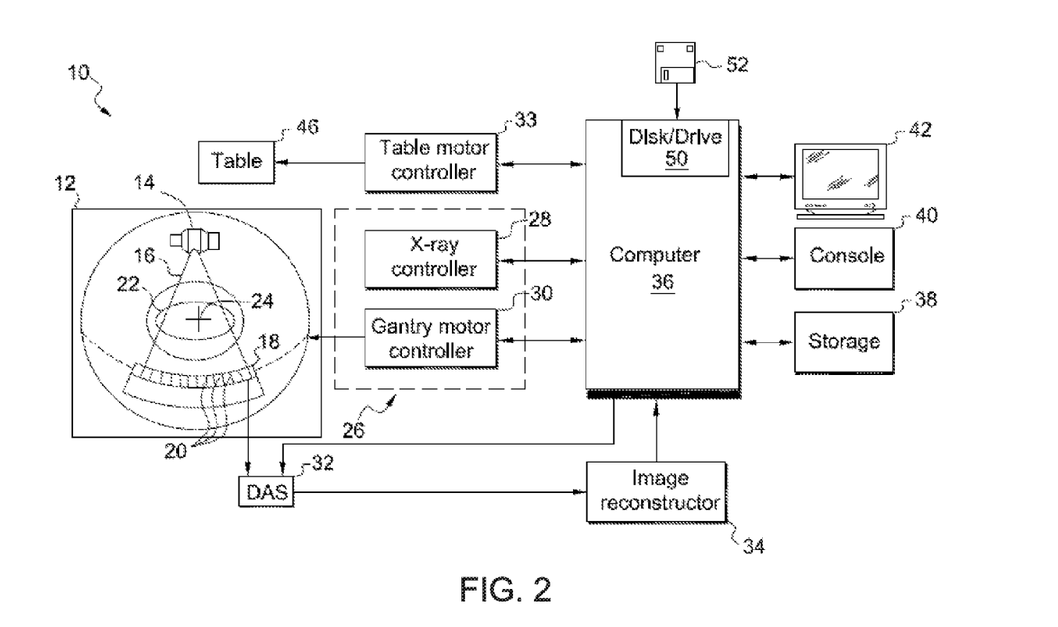
FIG. 2 is a block diagram representation of a CT imaging system as seen in FIG. 1.

With the preceding in mind, and referring to FIGS. 1 and 2, in these figures a multi-slice scanning imaging system, for example, a Computed Tomography (CT) imaging system 10, is shown as including a gantry 12 representative of a "third generation" CT imaging system. Gantry 12 has an X-ray tube 14 (also called X-ray source 14 herein) that projects a beam of X-rays 16 toward a detector array 18 on the opposite side of gantry 12. Detector array 18 is formed by a plurality of detector rows including a plurality of sensors 20 which together sense the projected X-rays that pass through an object, such as a medical patient 22, between array 18 and source 14. Each sensor 20 produces an electrical signal that represents the intensity of an impinging X-ray beam and hence can be used to estimate the attenuation of the beam as it passes through object or patient 22.

During a scan to acquire X-ray projection data, gantry 12 and the components mounted therein rotate about a center of rotation 24. FIG. 2 shows only a single row of sensors 20 (i.e., a detector row), typically produced as separate, discrete, and insertable detector modules. However, multi-slice detector array 18 includes a plurality of parallel detector rows of sensors 20 such that projection data corresponding to a plurality of quasi-parallel or parallel slices can be acquired simultaneously during a scan.

Rotation of components on gantry 12 and the operation of X-ray source 14 are governed by a control mechanism 26 of CT system 10. Control mechanism 26 includes an X-ray controller 28 that provides power and timing signals to X-ray source 14 and a gantry motor controller 30 that controls the rotational speed and position of components on gantry 12. A data acquisition system (DAS) 32 may be connected to receive analog signals from sensors 20 and convert the analog signals to digital signals for subsequent processing. An image reconstructor 34 receives sampled and digitized X-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). As used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to any suitable electronic system, imaging or otherwise, which utilizes flexible circuitry disposed on an underlying substrate.

A transducer broadly refers to a device for converting a signal in a given physical form, such as radiation, sound, temperature, pressure, light or other physical form to (or from) an electrical signal. In an example embodiment, a sensor array may include a plurality of transducers configured to receive an input signal in a given physical form and transmit a desired electrical output signal. For example, a transducer array may include a plurality of sensor devices, such as a photodiode, a back-illuminated photodiode, a sonic sensor, i.e. a sensor configured to detect sounds, a temperature sensor, and an electromagnetic radiation sensor. For present purposes, the basic concept being that a sensor array regardless of its specific implementation may generally employ an electrical interface to supply the signals sensed by the array.

Figure 3:
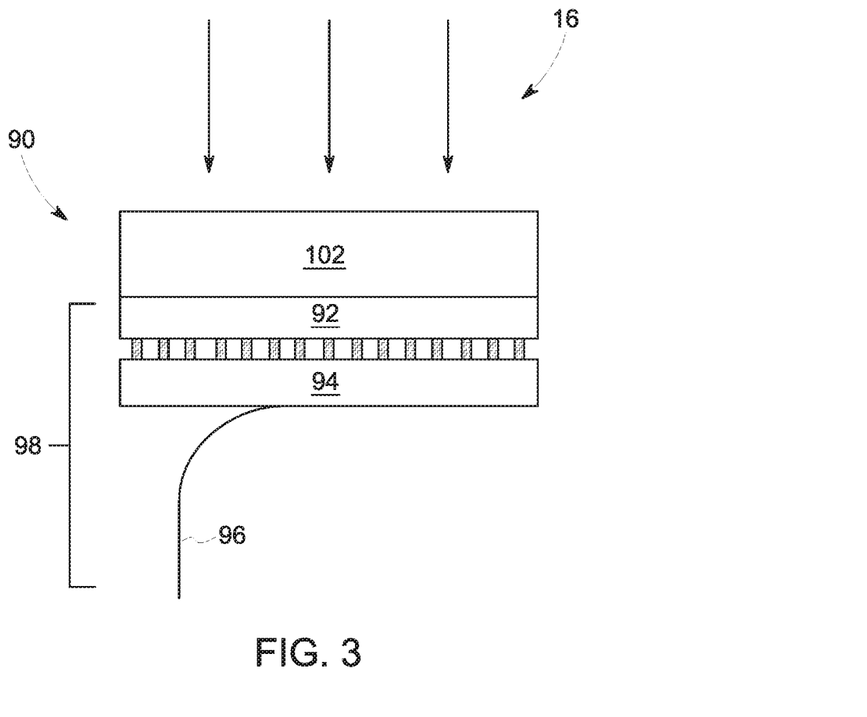
FIG. 3 depicts components of a detector element, in accordance with aspects of the present disclosure.

Referring now to FIG. 3, a block diagram of certain components of a modular detector element 90, such as may be used in forming detector array 18 and operating in accordance with certain aspects of the present disclosure, is illustrated. The modular detector element 90 is generally representative of a practical implementation of a single modular radiation detection and readout module which can be combined with other like modules to make a larger detector surface of any suitable size, such as for package, baggage, passenger, or patient screening or for industrial quality control applications. As discussed herein the detector element 90 may include a variety of electrical and structural features, and the simplified block view of FIG. 3 should not be construed as necessarily being indicative of particular spatial, geometric, electrical, or structural relationships between components. Indeed, as discussed herein, the discretely illustrated photodetection elements 92, ASIC 94, and readout lines 96 (i.e., the electrical circuitry or circuit components) may all be provided as part of a single flexible circuit (i.e., flex circuit) component 98, which is aligned on a substrate, discussed below, in forming the module 90.

With this in mind, and turning back to FIG. 3, during operation, radiation 16 (e.g., X-rays) from an imaging source 14 impinges on a scintillator 102 after being attenuated by an intervening subject or object undergoing imaging. Typically, the scintillator 102 is formed from a substance that interacts with the incident radiation 16 (for example X-ray photons) and in response emits light of a characteristic wavelength, such as an optical wavelength. The light emitted by the scintillator is, in turn detected by a photodetector layer 92, e.g., one or more photodiodes.

In operation, the photodetector layer 92 generates analog electrical signals in response to the light emitted by the scintillator 102. The electrical signals generated by the photodetector layer 92 are read out by signal electronics 94. In one such embodiment, the signal electronics 94 is provided as one or more chips or application specific integrated circuits (ASICs) (i.e., silicon packages) directly connected to photodiodes of the photodetector layer 92. In such an embodiment, the ASICs may convert the analog signals generated at the photodiodes to digital signals for subsequent processing. The signals from the signal electronics 94 (e.g., digitized signals) may in turn be communicated to downstream data acquisition circuitry, such as by lead or connector 96. The acquired signals are supplied to data processing circuitry and/or to image reconstruction circuitry.

In certain arrangements, the analog signals generated by the photodetector layer 92 are readout by signal electronics 94 provided on the detector module 90 and, as discussed herein, present in the same flexible circuit component 98. To protect the signal electronics 94 portion of the flexible circuit 98, it may be desirable to position the signal electronics 94 out of the path of (or minimize the profile of the signal electronics 94 with respect to) any radiation (e.g., X-rays 16) that is not converted by the scintillator 102 or otherwise absorbed. In this way, the electronics performing the analog-to-digital signal conversion and any additional processing are protected from incidental radiation that is not absorbed and converted by the scintillator 102.

As discussed in greater detail below, in certain embodiments, this may involve positioning the flex circuit 98 of a substrate such that the photodetector 92 portion of the flex circuit in on a surface of the substrate facing the radiation 100 while the signal electronics 94 is instead on a side surface of the substrate below and generally perpendicular to the radiation-facing surface, thus reducing the exposure of the signal electronics 94 to the incident radiation 16. As noted above, however, such a topographic arrangement may not be easily manufactured, as fabrication tools do not generally allow for the placement and/or lamination of a die on the side of a substrate being worked.

With the preceding in mind, the present approach describes the use of a reconfigurable substrate that may be configured one way during lamination of the flexible circuit to the substrate and may be configured another way for installation into a device being fabricated. Thus, in one example, a first configuration of the substrate is substantially or generally planar and, thus, suitable for handling using conventional tools that can be used to laminate the flexible circuit to the desired surfaces as well as bonding of the ASICs to the flexible circuit. The second configuration corresponds to the topology to be used in operation in the final product or device, such as a radiation detector, an ultrasound transducer, or a magnetic resonance coil arrangement. Therefore, using the reconfigurable substrate, a flexible circuit may be applied to the substrate which, in use, positions a circuitry component (e.g., an analog-to-digital ASIC in a detector context) on a side-facing facet(s) of the substrate while a separate circuitry component (e.g., a photodiode array in a detector context) may be placed on the top facet of the substrate.

In addition, with respect to certain of the embodiments described below, specific design features may be provided to facilitate reconfiguration of the substrate, to avoid of damage to the ASICs, to provide ratcheting or other locking mechanism(s) for a given configuration of the substrate, and/or to shield ASICs from high energy photons, electronic noise, and mechanical damage. In certain embodiments, the features of the reconfigurable substrate also facilitate incorporation of thermal structures such as heat pipes to improve overall device performance.

Figure 4:
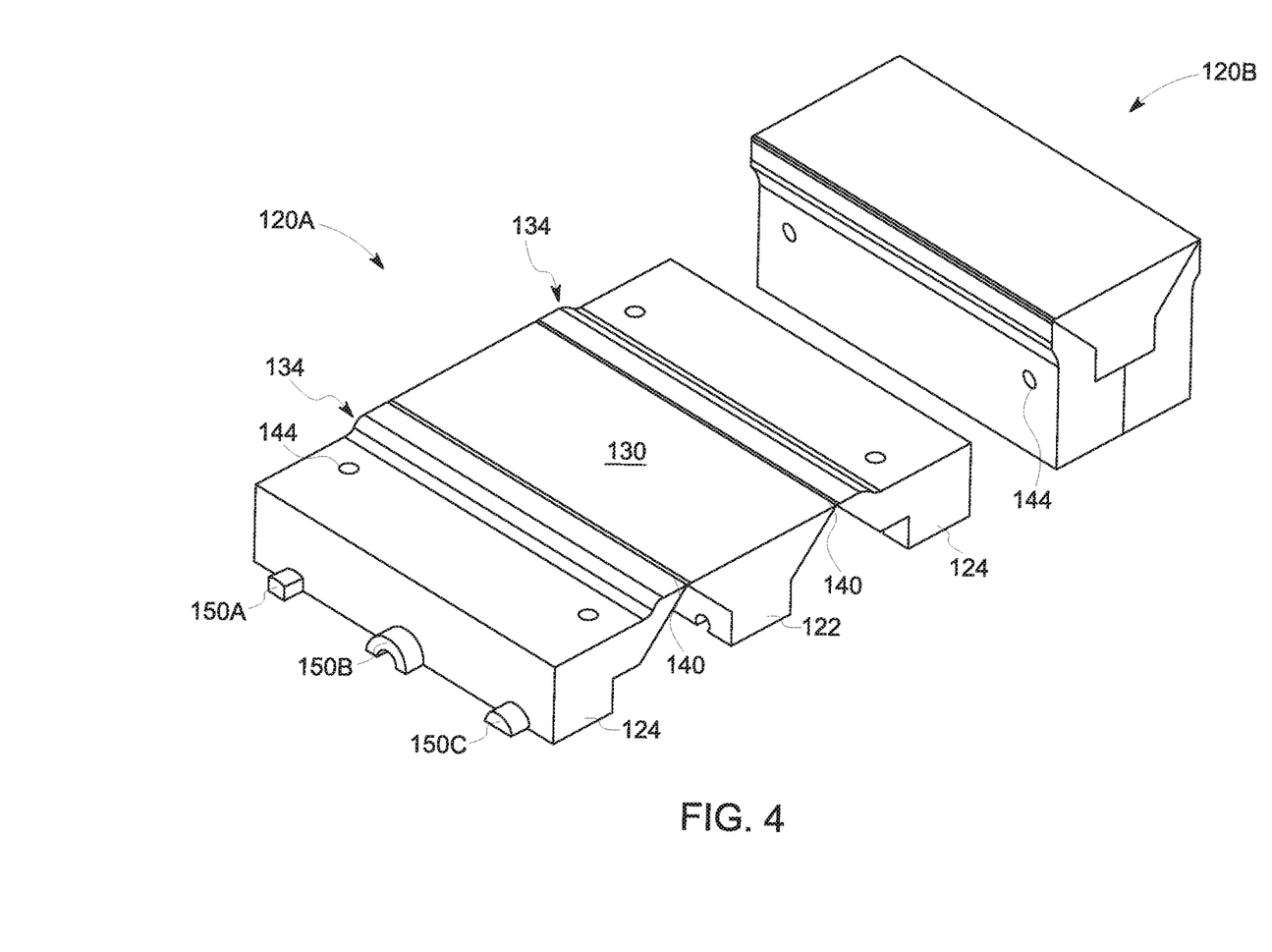
FIG. 4 depicts a perspective view of two configurations of an embodiment of an electronic substrate, in accordance with aspects of the present disclosure.

With the preceding comments in mind, one embodiment of a reconfigurable substrate 120 is depicted in FIG. 4, where a perspective view of the reconfigurable substrate 120 is shown in an open or substantially flat configuration (120A) on the lower left and in closed or folded configuration (120B) on the upper right. In the open configuration, the substrate 120A is sufficiently flat to fit within a fabrication tool, such as a laminator, which affixes a flex circuit and/or die to the respective upward facing surface of the open substrate 120A. In the depicted example, a center pedestal 122 has substantially the same height as the side legs 124 when in the open configuration, providing the generally flat top surface 130 for laminating when the substrate is in an open configuration and placed on a flat surface of the tool.

In the depicted example, when in the open configuration the substrate 120A is not entirely flat on the top surface 130 but may have slight changes in elevation 134 between the pedestal 122 and side legs 124. These elevation differences 130 are typically within the height tolerances allowed by the tool and, in the depicted example, provide a graded or shallow radiused drop-off in height (i.e., are not sharp transition angles) between the pedestal 122 and legs 124. Such sharp angles, if present, would be difficult to laminate in a conventional tool and may impose strain on the laminated flex circuit at these joint regions when the substrate 120 is in the second, closed configuration or moved to the folded configuration. Thus, the height differences and graded transition also served to reduce the strain imposed on the flex circuit in an operational state.

In the depicted example, movement of the substrate 120A from the open configuration to the folded configuration (i.e., substrate 120B) is structurally permitted by a pair of living hinges 140 situated between the pedestal 122 and legs 124. As will be appreciated, in such a living hinge arrangement, the laminated flex circuit may itself serve as the living hinge. In alternate embodiments, the material forming the substrate 120 may be constructed from a plastic or polymer such as nylon, ABS, or polyetherimide, and is locally formed thin enough so as to be flexible at the region of the hinge 140, thereby allowing the legs 124 to move with respect to the pedestal 122 and allowing the substrate 120 to be transitioned between the open and folded configurations. As will also be appreciated, in other embodiments, other types of hinging mechanisms may be employed, with the depicted living hinge mechanism provided merely as a non-limiting example. In embodiments where other types of mechanical hinging or assembly mechanisms are provided, the different components or pieces of the substrate 120 may be formed from different materials, for example the legs 124 may be formed from different materials than the pedestal 122.

The depicted example of a substrate also includes through-holes 144 that may serve a variety of purposes. In one implementation, the through-holes 144 may allow electrical connections to be formed through the substrate 120 when in the closed configuration 120B. Similarly, the through-holes 144 may allow for the insertion of lock pins or other similar structures when the substrate 120 is in the closed configuration 120B to lock the substrate 120B in the closed configuration. In addition, the through-holes 144 may also be used during the lamination process to position and align the flex circuit on the substrate and/or to evaluate the positioning of the flex circuit on the substrate 120 after lamination.

Further, the embodiment of the substrate 120 shown in FIG. 4 also includes a series of alignment features 150A (e.g., a flat-sided solid pin), 150B (e.g., a circular hollow pin), and 150C (e.g., a circular solid pin), with half of each feature 150 being present on each leg 124. Thus, in this example, when in the closed configuration 120B, the alignment features 150 are complete and may be used in guiding and aligning insertion of the folded substrate 120B into corresponding and complementary openings of an electronic device. By way of example, when the substrate 120 is a component of a detector module 90, the alignment features 150 may facilitate proper insertion of the detector module into an area detector device or assembly.

Figure 5:
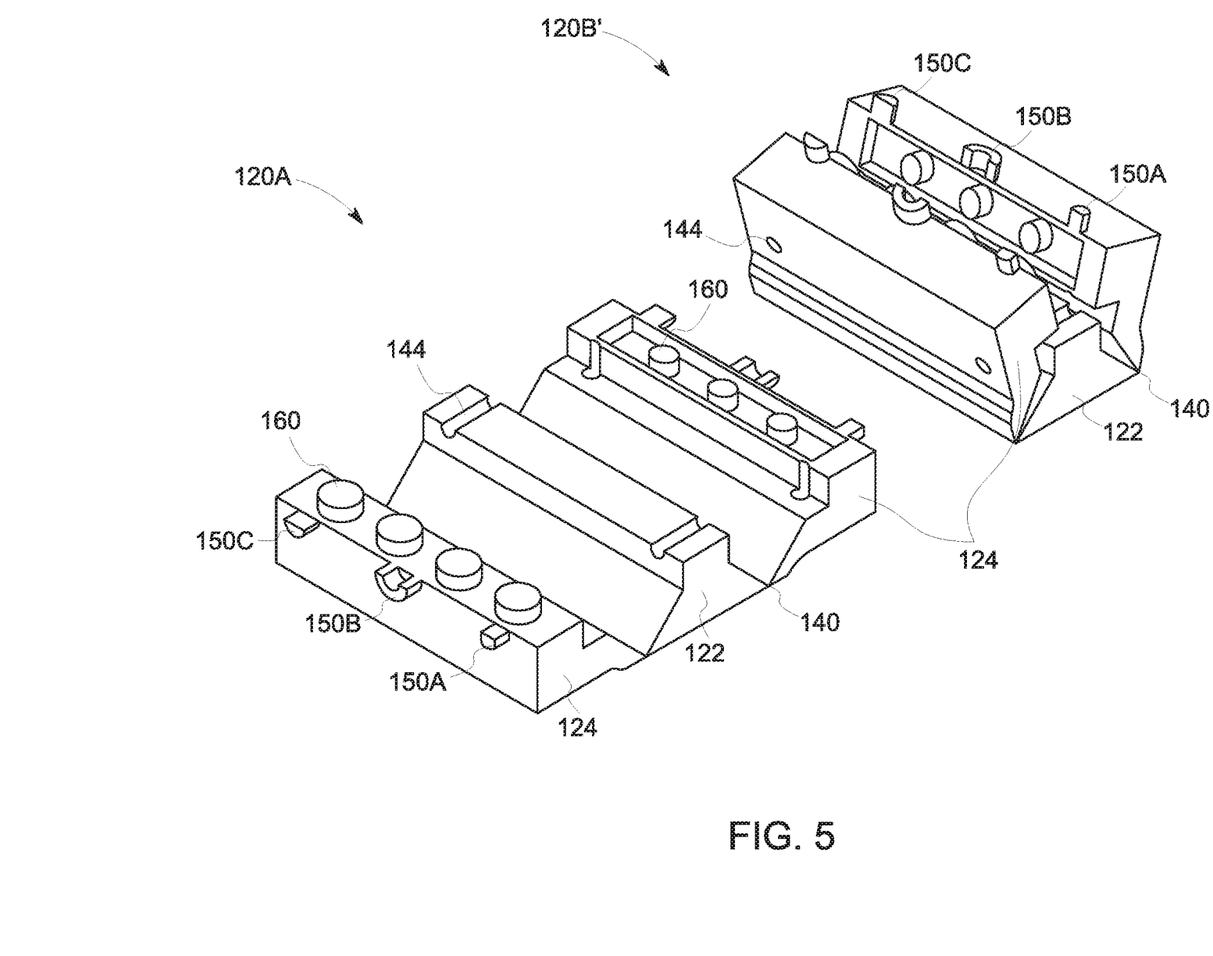
FIG. 5 depicts an alternative perspective view of the electronic substrate of FIG. 4, in accordance with aspects of the present disclosure.

Turning to FIG. 5, the substrate 120 of FIG. 4, including alignment features 150, can be seen from a reversed perspective. In FIG. 5, the depicted upper right configuration shows the substrate 120 in the process of folding, instead of fully folded, and thus is denoted substrate configuration 120B'. In addition to the features discussed with respect to FIG. 4, FIG. 5 also reveals a set of complementary features 160, here shown as interlocking posts of different sizes and spacing on the different respective legs 124. In the depicted example, the complementary features 160 interlock when the substrate is in the folded configuration 120B so as to hold or lock the substrate closed or folded. Further, in some implementations, a tool (e.g., a laminator) or fixture provided in the tool may also be provided with the corresponding complementary structures so that the substrate 120A may be interlocked with these features within the tool, thereby aligning and securing the substrate 120A within the tool during processing. As will be appreciated, inclusion of such complementary features is optional, and they may be absent from some embodiments.

Figure 6:
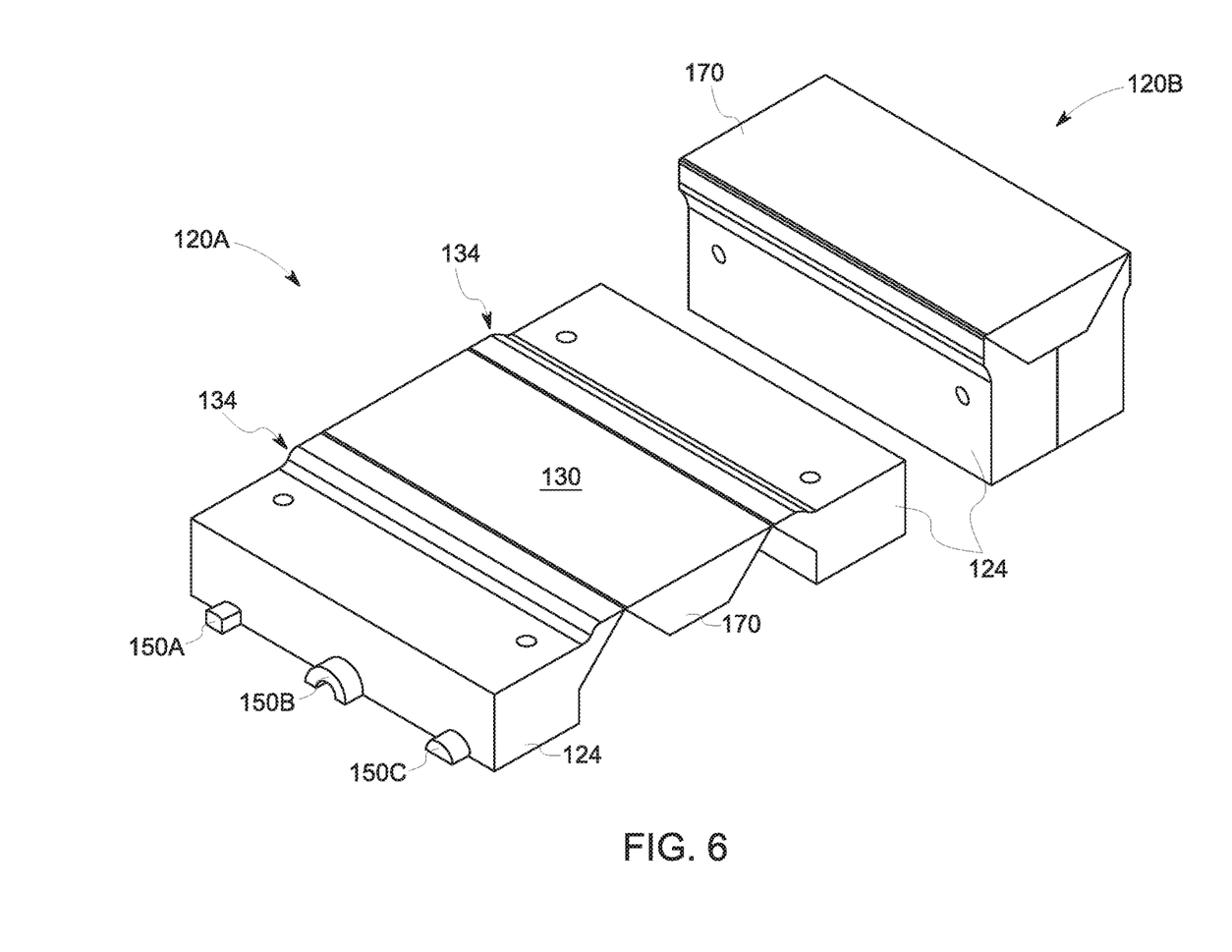
FIG. 6 depicts a perspective view of two configurations of a further embodiment of an electronic substrate, in accordance with aspects of the present disclosure.

Turning to FIG. 6, a further embodiment is depicted in which the central piece, (i.e., shallow pedestal 170) is shallow relative to the legs 124. In such an embodiment, the substrate 120A, when in an open configuration, may employ a form or other assembly fixture when positioned in a tool (such as a laminator) to accommodate the shallow pedestal 170 relative to the longer legs 124. An embodiment, as shown in FIG. 6 may be useful in certain instances, such as where the substrate 120 components are constructed of different materials (i.e., a composite construction) and the material used to construct the pedestal 170 is more expensive or disproportionately denser than the material used to construct the legs 124. For example, in some embodiments, the pedestal 170 may be made from or incorporate tungsten or other high Z materials to provide radiation shielding to underlying components.

Figure 7:
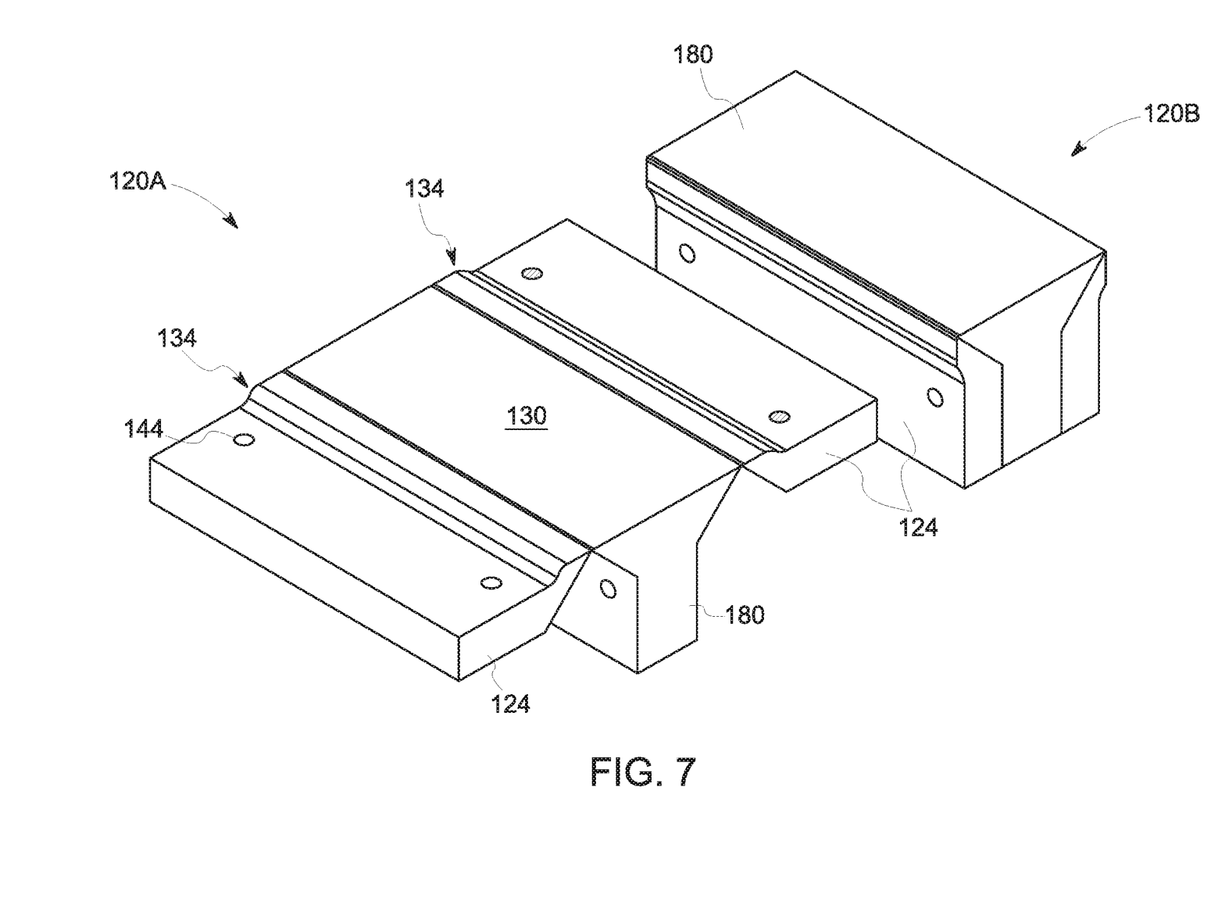
FIG. 7 depicts a perspective view of two configurations of another embodiment of an electronic substrate, in accordance with aspects of the present disclosure.

Turning to FIG. 7, an additional embodiment is depicted in which the central piece, (i.e., deep pedestal 180) extends downward to the same extent as the legs 124 when in the folded configuration 120B. In such an embodiment, the substrate 120A, when in an open configuration, may employ a form or other assembly fixture when positioned in a tool (such as a laminator) to accommodate the deeper pedestal 180 relative to the legs 124. One advantage of the deep pedestal 180 is that alignment features 150 disposed on the base of the deep pedestal 180 (i.e., opposite face 130) do not need to be split, as in the preceding embodiments. This may be a benefit with respect to assembly of the final device and/or with respect to manufacturing tolerances.

Figure 8:
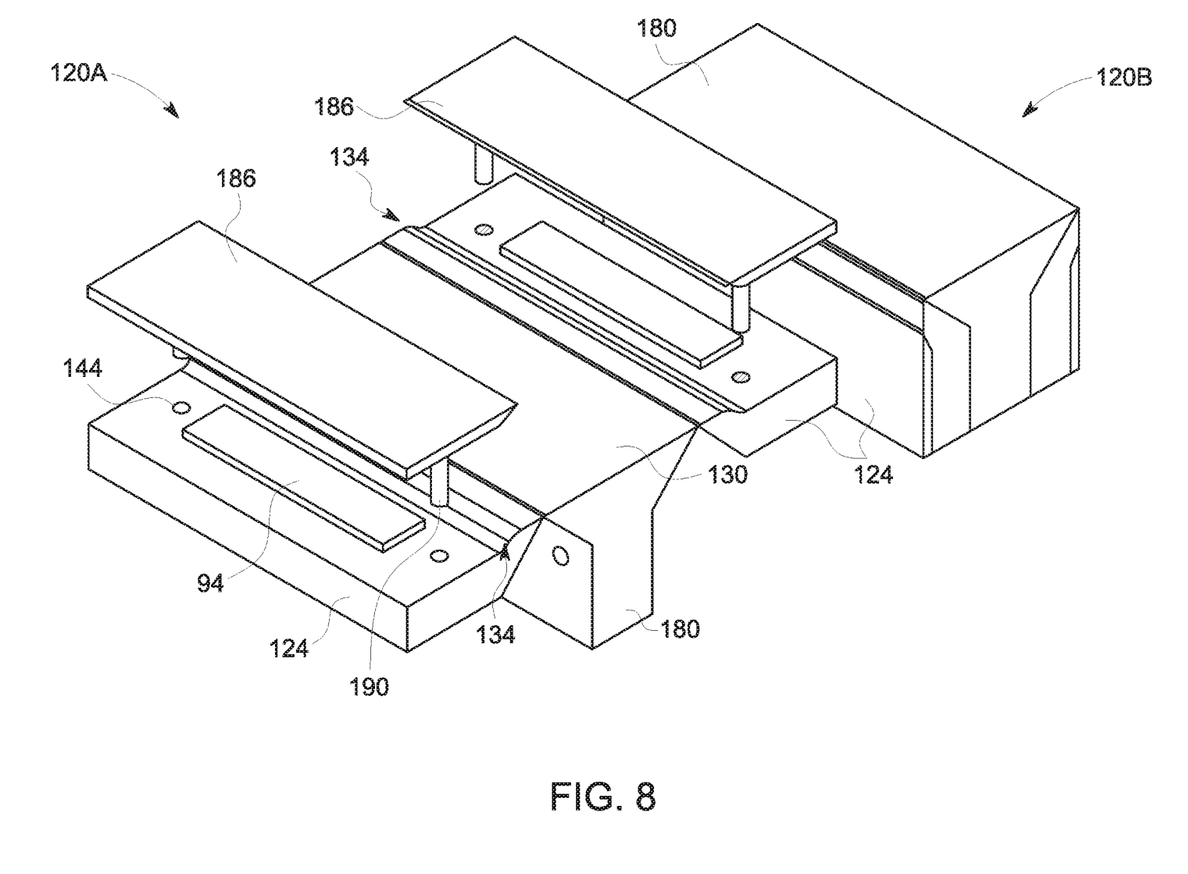
FIG. 8 depicts the electronic substrate of FIG. 7 with optional protective side covers, in accordance with aspects of the present disclosure.

Turning to FIG. 8, the embodiment of FIG. 7 is shown in conjunction with separate protective covers 186 (in addition to the underlying signal electronics 94 (e.g., ASICs). In one embodiment, the protective covers are formed from a radiation blocking or absorbing material (e.g., Tungsten) and may include features 190 or legs for engaging the through-holes 144, thus shielding the underlying ASICs when attached. As will be appreciated, engagement of features 190 with through-holes 144 may also afford paths for electrical and/or thermal conduction to optimize the performance of signal electronics 94. In the depicted example, the protective covers 186 have a height corresponding to the elevation drop-off 134 between the pedestal 180 and legs 124 when in the open configuration 120A. Thus, when attached and the substrate 120 is in the folded configuration, the protective covers 186 provide a straight line or edge to the side of the folded substrate 120B.

Figure 9:
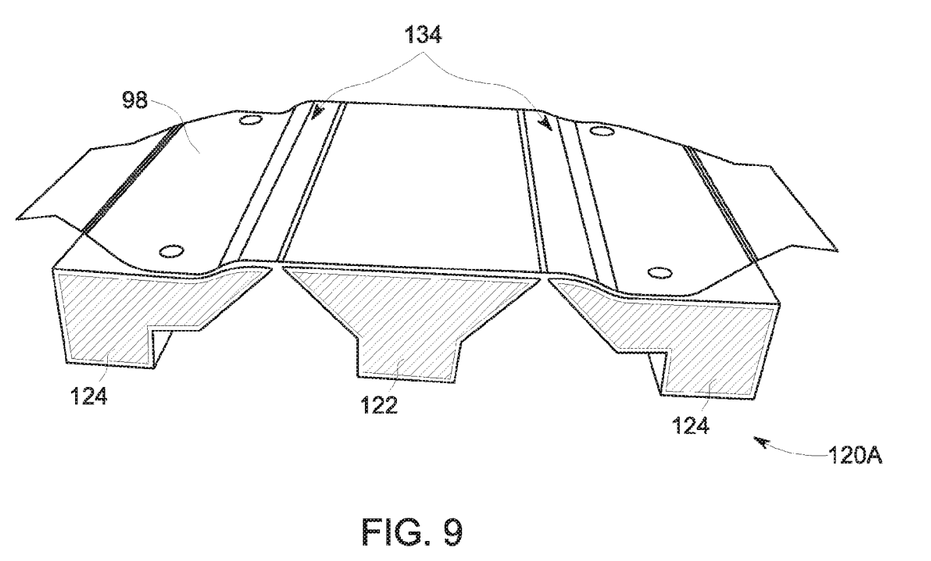
FIG. 9 depicts an embodiment of an electronic substrate and attached flexible element in an open configuration, in accordance with aspects of the present disclosure.
Figure 10:
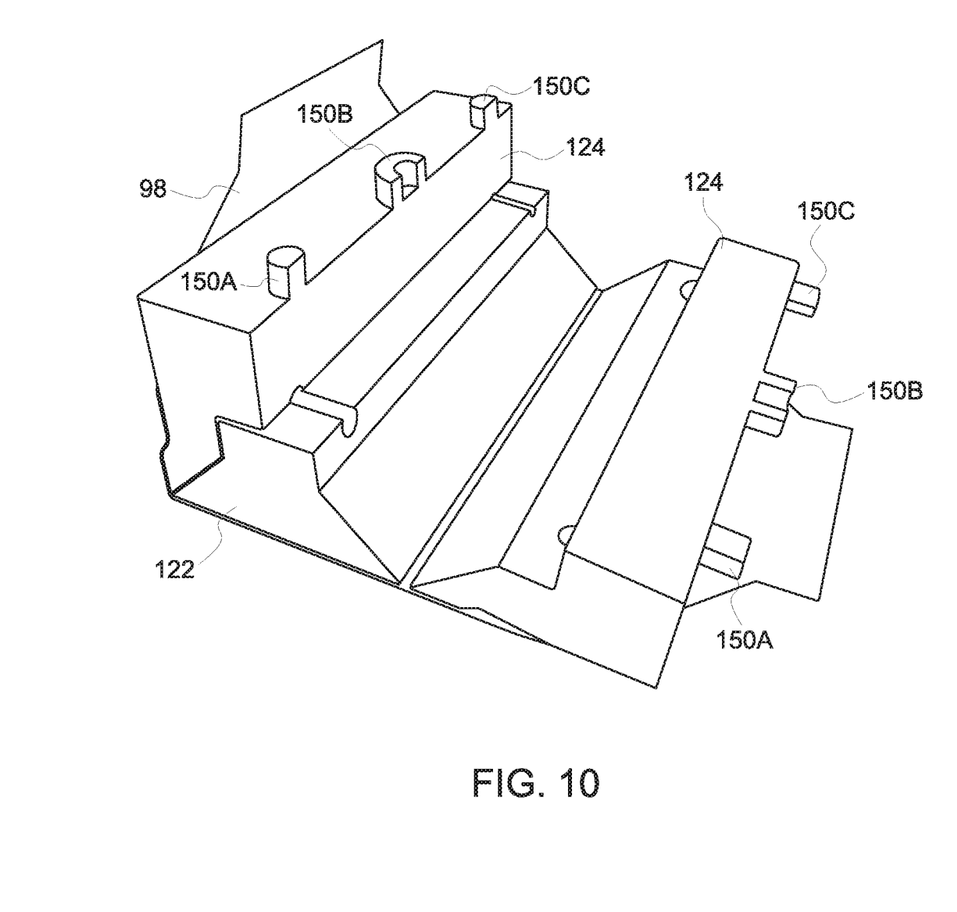
FIG. 10 depicts the electronic substrate and attached flexible element of FIG. 9 in the process of being folded or closed, in accordance with aspects of the present disclosure.
Figure 11:
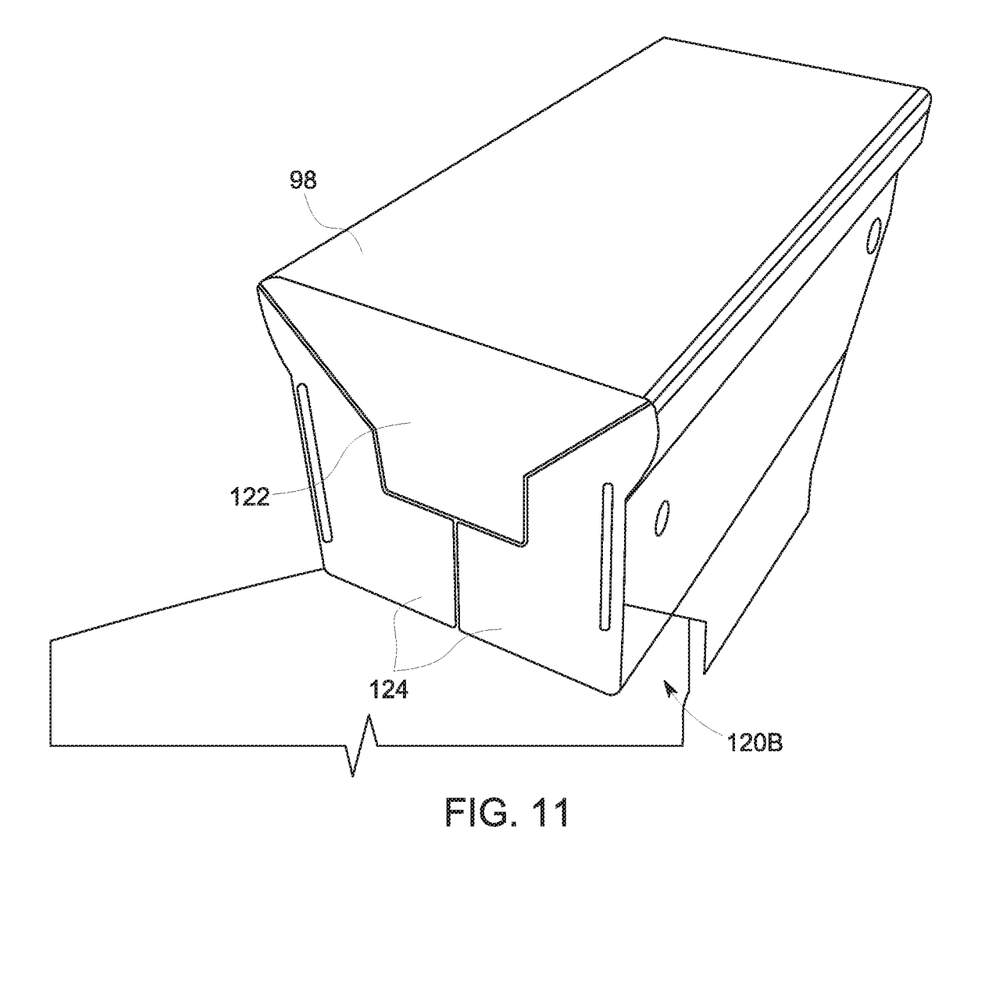
FIG. 11 depicts the electronic substrate and attached flexible element of FIG. 9 in a folded or closed configuration, in accordance with aspects of the present disclosure.

Turning to FIGS. 9-11, an example of a substrate 120 (in particular, the embodiment of the substrate 120 discussed with respect to FIGS. 4 and 5 is shown in conjunction with a flexible substrate (e.g., a flex circuit 98) attached to the substrate 120 through various stages of a fabrication process. As shown in FIG. 9, the substrate 120A is shown in an open configuration in which the pedestal 122 and legs 124 form a substantially planar or flat surface on which the flex circuit 98 is attached, such as by lamination. Turning to FIG. 10, the substrate 120 is shown partially folded after attachment of the flex circuit 98. That is, FIG. 10 shows an intermediate configuration between the open and folded configurations of the substrate 120. Turning to FIG. 11, the substrate 120B, with attached flex circuit 98, is shown in a closed or folded configuration, presumably ready for attachment to a larger electronic device.

While the preceding related examples suitable for use in various devices, including, but not limited to, radiation detectors and ultrasound transducers, it should be appreciated that the configurations and structures described herein are provided for illustration only and are not intended to be limiting. In particular, the form or geometry of the underlying substrate is not limited to the configurations discussed herein and may be essentially arbitrary, depending on the application specific need. For example, substrate structures may be provided that include folding substrate elements across multiple, oblique axes. In such an implementation, taper angles on the recessed faces of the substrate elements determine the resulting geometry of the reconfigured substrate. By way of example, in a magnetic resonance imaging system context, a substrate may be provided which is generally flat in a first configuration, such as for attachment of an RF or electrical coil, but which, when folded, conforms to an anatomical part (e.g., a head, a hand, a foot, an arm, a torso, and so forth) so as to provide a coil assembly that is easy to assemble (in its flat configuration) but conforms to an anatomic region in a folded configuration.

Technical effects of the invention include fabrication of a multi-component circuit device such that the circuit device is fabricated and assembled in a planar configuration and subsequently reconfigured into a three-dimensional form with precise alignment of mechanical features. In this manner, the process enables fabrication of modular electronics designs having significantly greater complexity than currently available.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. An electronic module, comprising:
a first component having a first planar surface;
one or more additional components rotatably attached to the first component, wherein each additional component comprises a second planar surface that is generally parallel to the first planar surface in a first configuration of the electronic module and is not parallel to the first planar surface in a second configuration of the electronic module; and
a flexible circuit laminated to both the first planar surface and the second planar surfaces, wherein the flexible circuit comprises a first electrical component positioned over the first planar surface and a second electrical component positioned over at least one of the second planar surfaces such that, in the first configuration, the first electrical component and the second electrical component are generally parallel to one another and in the second configuration, the first electrical component and the second electrical component are not parallel to one another.

2. The electronic module of claim 1, wherein the first component comprises a center pedestal component and the one or more additional components comprise two side leg components, each connected to opposite sides of the center pedestal component by living hinges.

3. The electronic module of claim 2, wherein the two side leg components, when in the second configuration, cover a surface of the center pedestal component opposite the first planar surface.

4. The electronic module of claim 3, wherein each side leg component comprise a complementary half of one or more alignment features such that, when in the second configuration, the alignment features are present on a surface opposite the first planar surface.

5. The electronic module of claim 2, wherein the center pedestal component, when in the second configuration, extends downward from the first planar surface to the same extent as the two side leg components.

6. The electronic module of claim 5, wherein one or more alignment features are provided on a surface of the center pedestal component opposite the first planar surface.

7. The electronic module of claim 1, further comprising one or more alignment features that are present on a surface opposite the first planar surface at least when the electronic module is in the second configuration.

8. The electronic module of claim 1, wherein the first planar surface and the second planar surfaces, when in the first configuration, are vertically offset from one another.

9. The electronic module of claim 1, wherein the first electrical component of the flexible circuit comprises photodetector circuitry and wherein the second electrical component comprises signal readout electronics.

10. The electronic module of claim 1, wherein the first component is formed primarily of a first material and the one or more additional components are formed primarily of a second material different from the first material.

11. The electronic module of claim 1, further comprising one or more protective covers attached to the one or more additional components so as to cover all or part of the second planar surfaces when attached.

12. The electronic module of claim 1, further comprising one or more locking features formed at least on the one or more additional components, wherein the one or more locking features engage to hold the electronic module closed when in the second configuration.

13. A method for fabricating an electronic module, comprising:
placing an electronic substrate that is in a first configuration into a laminator tool, wherein the electronic substrate comprises a first planar surface and a second planar surface that are generally parallel to one another when in the first configuration;

positioning a flexible circuit on the electronic substrate such that a first circuitry of the flexible circuit is on the first planar surface and a second circuitry of the flexible circuit is on the second planar surface;

laminating the flexible circuit onto the electronic substrate;

removing the electronic substrate from the laminator tool; and reconfiguring the electronic substrate into a second configuration in which the first planar surface and the second planar surface are not parallel to one another.

14. The method of claim 13, wherein the placing the electronic substrate into the laminator tool comprises placing the electronic substrate into an assembly fixture that compensates for height differences between portions of the electronic substrate underlying the first planar surface and the second planar surface.

15. The method of claim 13, wherein the reconfiguring the electronic substrate comprises engaging locking features provided on the electronic substrate.

16. The method of claim 13, wherein the first circuitry of the flexible circuit comprises photodetection circuitry and the second circuitry comprises signal electronics.

17. The method of claim 13, comprising placing the electronic substrate, when in the second configuration, into an electronic device using alignment features present on the electronic substrate when in the second configuration.

18. An imaging system, comprising:
a signal detection component comprising one or more detector modules, wherein each detector module comprises:
an electronic substrate movable between at least a first configuration and a second configuration, wherein the first configuration has two or more planar surfaces that are generally parallel to one another while in the second configuration the two or more planar surface are not parallel to one another;
a flex circuit laminated onto the electronic substrate, wherein the flex circuit is laminated onto the two or more planar surfaces; and
one or more alignment features present on the electronic substrate that mate with complementary features present in an interface with the signal detection component.

19. The imaging system of claim 18, wherein the signal detection component comprises one of a radiation detector, an ultrasound transducer, or a magnetic resonance imaging coil.

20. The imaging system of claim 18, wherein the flex circuit comprises different circuitries positioned over each of the respective two or more surfaces.

* * * * *